US010952795B2

(12) United States Patent
Cohen et al.

(10) Patent No.: US 10,952,795 B2
(45) Date of Patent: Mar. 23, 2021

(54) SYSTEM AND METHOD FOR GLASS STATE VIEW IN REAL-TIME THREE-DIMENSIONAL (3D) CARDIAC IMAGING

(71) Applicant: Biosense Webster (Israel) Ltd., Yokneam (IL)

(72) Inventors: Benjamin Cohen, Haifa (IL); Natan Sharon Katz, Atlit (IL); Lior Zar, Poria Illit (IL); Oshrat Ben Zaken, Shimshit (IL); Dror Berman, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 412 days.

(21) Appl. No.: 15/638,886

(22) Filed: Jun. 30, 2017

(65) Prior Publication Data

US 2019/0000540 A1   Jan. 3, 2019

(51) Int. Cl.
*A61B 34/20* (2016.01)
*A61B 5/06* (2006.01)
(Continued)

(52) U.S. Cl.
CPC .............. *A61B 34/20* (2016.02); *A61B 1/05* (2013.01); *A61B 5/015* (2013.01); *A61B 5/065* (2013.01);
(Continued)

(58) Field of Classification Search
CPC . A61B 18/1477; A61B 18/1492; A61B 5/044; A61B 5/015; A61B 5/0402;
(Continued)

(56) References Cited

U.S. PATENT DOCUMENTS 4,985,834 A * 1/1991 Cline ...................... G06T 17/00
345/424
2004/0097805 A1   5/2004 Verard et al.
(Continued)

FOREIGN PATENT DOCUMENTS

EP   2077526A2 A2   7/2009
JP   2012170777 A   9/2012

OTHER PUBLICATIONS

Zhang, Lei, et al. GPU-based Fusion Method for 3D Electrophysiological Data Visualization [online], IEEE, Dec. 2012 [added to IEEE Xplore on Jan. 27, 2014, retrieved on Oct. 7, 2019], Electronic ISBN: 978-1-4673-5129-4. Retrieved from the Internet: [URL: see Office action], (Year: 2012).*
(Continued)

*Primary Examiner* — Patricia J Park
*Assistant Examiner* — Victoria Fang (57) ABSTRACT

As part of a real-time three-dimensional (3D) cardiac imaging system and method, anatomical data of a cardiac structure may be acquired and a 3D model of the cardiac structure may be generated. Visual data relevant to a cardiac procedure may be generated, such as location and orientation of a catheter, tags, points, color-coded temperature information, and/or color-coded local activation times (LAT) for the cardiac structure. The visual data superimposed on the 3D model of the cardiac structure may be visually displayed on a visual display device. A glass state view may be generated by generating a modified set of the visual data that includes removing at least a portion of the visual data that obscures a view of an anatomical feature of interest and/or the catheter, and adding edge enhancement to the cardiac structure. The glass state view may be requested to be visually displayed on the visual display device.

18 Claims, 8 Drawing Sheets
(2 of 8 Drawing Sheet(s) Filed in Color)

(51) Int. Cl.
*A61B 5/01* (2006.01)
*G06T 19/20* (2011.01)
*G06T 19/00* (2011.01)
*A61B 5/318* (2021.01)
*A61B 5/339* (2021.01)
*A61B 90/00* (2016.01)
*A61B 34/10* (2016.01)
*A61B 18/00* (2006.01)
*A61B 18/14* (2006.01)
*A61B 1/05* (2006.01)

(52) U.S. Cl.
CPC .............. *A61B 5/318* (2021.01); *A61B 5/339* (2021.01); *A61B 18/1477* (2013.01); *A61B 34/10* (2016.02); *A61B 90/37* (2016.02); *G06T 19/006* (2013.01); *G06T 19/20* (2013.01); *A61B 2018/00351* (2013.01); *A61B 2018/00577* (2013.01); *A61B 2034/105* (2016.02); *G06T 2207/20172* (2013.01); *G06T 2207/20192* (2013.01); *G06T 2207/30048* (2013.01); *G06T 2210/41* (2013.01); *G06T 2219/2012* (2013.01); *G06T 2219/2024* (2013.01)

(58) Field of Classification Search
CPC ......... A61B 5/0452; A61B 5/065; A61B 1/05; A61B 2018/00351; A61B 2018/00577; A61B 2034/2065; A61B 2034/105; A61B 90/37; A61B 90/361; A61B 34/20
USPC .......... 600/424; 382/163, 266, 274; 345/426
See application file for complete search history.

(56) References Cited

U.S. PATENT DOCUMENTS

| | | |
|---|---|---|
| 2004/0153128 A1 | 8/2004 | Suresh |
| 2006/0253032 A1 | 11/2006 | Altmann et al. |
| 2008/0219540 A1* | 9/2008 | Ter Mors ................ G06T 15/08 382/132 |
| 2008/0234570 A1* | 9/2008 | Gerard ..................... A61B 6/12 600/424 |
| 2009/0177089 A1* | 7/2009 | Govari ..................... A61B 8/12 600/453 |
| 2009/0264738 A1* | 10/2009 | Markowitz .......... A61B 5/0422 600/424 |
| 2011/0144524 A1 | 6/2011 | Fish et al. |
| 2013/0296845 A1* | 11/2013 | Bar-Tai .................... A61N 1/06 606/34 |
| 2016/0104312 A1* | 4/2016 | Zino ....................... A61B 6/52 345/427 |
| 2016/0155274 A1* | 6/2016 | Merschon ............... G06T 19/20 345/419 |

OTHER PUBLICATIONS

Obermeier, Barbara, and Ted Padova. Hide and Show Layers in Photoshop Elements 11 [online]. Dummies, Feb. 11, 2017 [ retrieved on Oct. 9, 2019], Retrieved from the Internet: [URL: see Office action], (Year: 2017).*

Borland, David, and Russell M. Taylor II. Rainbow Color Map (Still) Considered Harmful [online], IEEE Computer Graphics and Applications, Mar. 5, 2007 [retrieved on Sep. 25, 2019], vol. 27, No. 2, pp. 14-17. Retrieved from the Internet: [URL/DOI: see Office action], (Year: 2007).*

P.S. Hiremath & Kodge B.G., An Effect of Spatial Filtering in Visualization of Coronary Arteries Imaging, International Journal of Computer Science & Information Technology, 2009, vol. 2, No. 1, Serials Publications, New Delhi.

Extended European Search Report dated Nov. 20, 2020 for European Patent Application No. 20198151.1.

Jansen, "The Graphical User Interface: An Introduction." (1998).

* cited by examiner

LUMINOSITY ADDITION = K / |(N dot V)|
LOW ADDITION

FIG. 4B

LUMINOSITY ADDITION = K / |(N dot V)|
HIGH ADDITION

SYSTEM AND METHOD FOR GLASS STATE VIEW IN REAL-TIME THREE-DIMENSIONAL (3D) CARDIAC IMAGING

SUMMARY

A real-time three-dimensional (3D) cardiac imaging system and method are disclosed. Anatomical data of a cardiac structure may be acquired and a 3D model of the cardiac structure may be generated. Visual data relevant to a cardiac procedure may be generated, such as location and orientation of a catheter, tags, points, color-coded temperature information, and/or color-coded local activation times (LAT) for the cardiac structure. The visual data superimposed on the 3D model of the cardiac structure may be visually displayed on a visual display device. A glass state view may be generated by generating a modified set of the visual data that includes removing at least a portion of the visual data that obscures a view of an anatomical feature of interest and/or the catheter, and adding edge enhancement to the to the 3D model of cardiac structure.

Generating the edge enhancement may include calculating a luminosity value (e.g., a white addition) based on the view path and adding it the value of each respective point of the 3D model of the cardiac structure. The glass state view may be requested by an operator, for example via an operator interface, to be visually displayed on the visual display device. The modified set of visual data may maintain some or all of the color-coded temperature information, and/or may convert color-coded temperature information to grey-scale or shaded, low-density coloring. The modified set of visual data may maintain the location and orientation of the catheter and/or remove the points and the tags from the visual data. Two or more different glass state views may be available containing different modified sets of the visual data.

BRIEF DESCRIPTION OF THE DRAWINGS

The patent or application file contains at least one color drawing or photograph as a drawing executed in color. Copies of this patent or patent application publication with color drawing(s) will be provided by the Office upon request and payment of the necessary fee.

DETAILED DESCRIPTION OF THE EMBODIMENTS

Cardiac ablation is a medical procedure performed by electrophysiologists that may be used to correct heart rhythm defects, known as arrhythmias, by creating lesions to destroy tissue in the heart that contributes to the rhythm defects. An example arrhythmia that can be treated using cardiac ablation is atrial fibrillation (AF), which is an abnormal heart rhythm that originates in the atria of the heart.

Cardiac ablation may employ long, flexible catheters (endoscope) that may be inserted through a small incision in the groin and through the blood vessels to the heart, and may be used to apply energy (e.g., radio frequency (RF) energy, or extreme cold) to produce small scars or lesions on the tissue to block faulty electrical impulses that may cause the heart rhythm disorders. Real-time three-dimensional (3D) location and mapping technology may be employed to visualize the exact position and orientation of a catheter within the heart and act as an advanced navigation system to enable the electrophysiologist to visualize and carefully guide the catheter to administer the RF energy in the appropriate locations. Goals of cardiac ablation are to remove the arrhythmia to return the patient's heart to a normal heart rhythm or reduce the frequency of arrhythmia and the severity of symptoms in the patient.

An example of a real-time 3D location and mapping system for cardiac ablation is the CARTO® 3 System, produced by Biosense Webster®, Inc., a subsidiary of Johnson & Johnson. The CARTO® 3 System uses electromagnetic technology to create 3D maps of a patient's cardiac structure and to display the exact location and orientation of the catheters (or other objects) in the heart. The CARTO® 3 System compensates for patient and cardiac motion to ensure accurate, real-time visualization of the cardiac structures.

Figure 1:
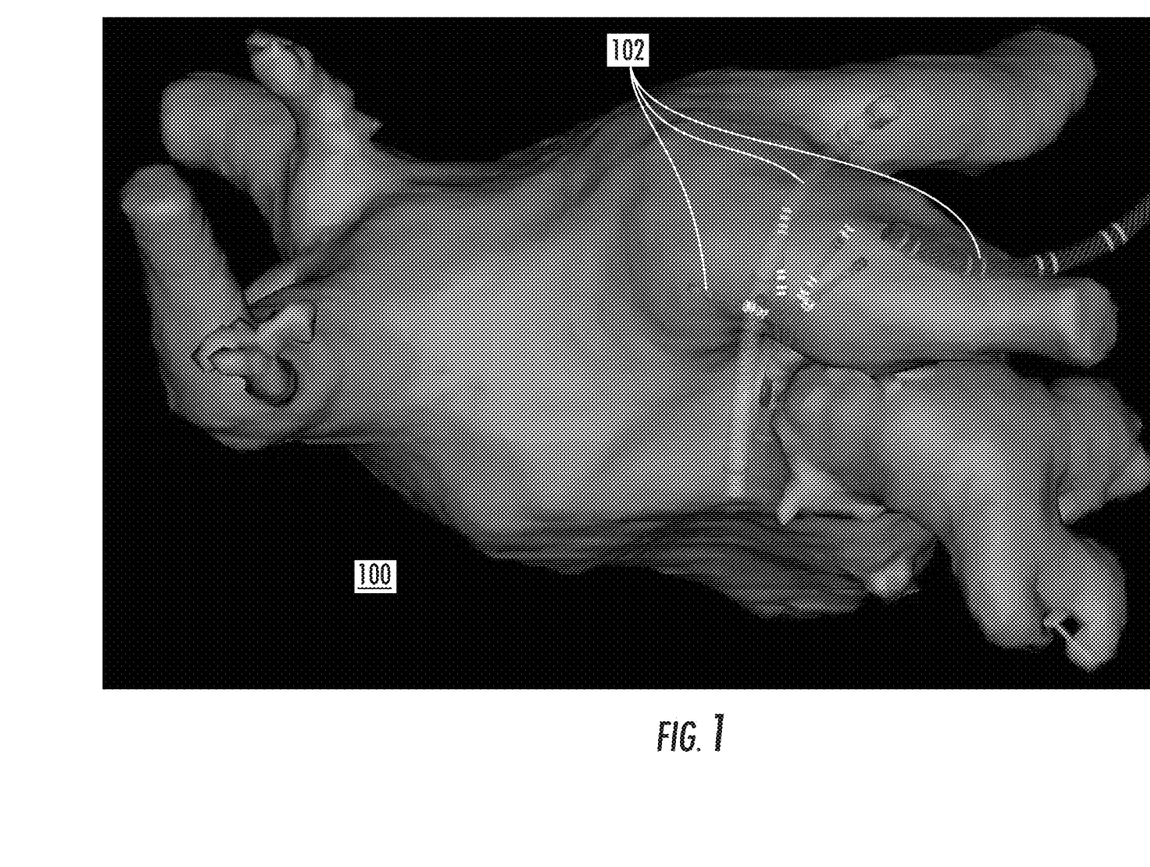
FIG. 1 is example three-dimensional (3D) cardiac map of a patient's heart generated by a CARTO® 3 System.

FIG. 1 is an example 3D cardiac map 100 of a patient's heart generated by a CARTO® 3 System. During a cardiac procedure, the location and orientation of one or more catheters 102 may be illustrated within the 3D cardiac map 100 of the heart. Other objects and images, although not shown, may be included in the 3D visualization shown in FIG. 1 such as, but not limited to, the following: the location and orientation of additional catheters and devices; a 3D synthetic heart model used for orientation within the mapped heart; a two-dimensional (2D) image to assist in directional (e.g., up, down, back, forward) orientation; and fluoroscopy images or other background images.

Figure 2A:
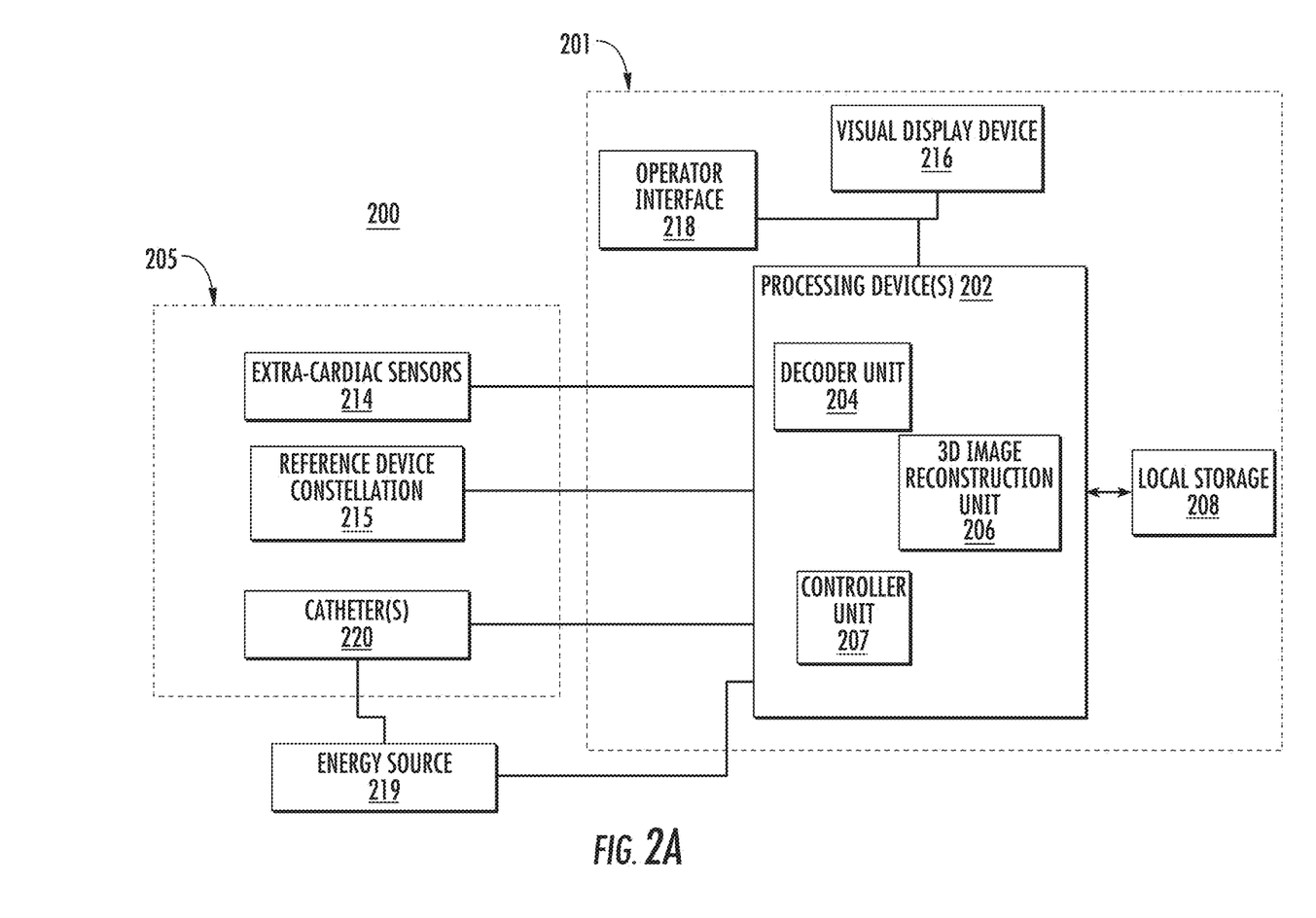
FIG. 2A is a schematic diagram of an example cardiac mapping and ablation system.

FIG. 2A is a schematic diagram of an example cardiac mapping and ablation system 200 with integrated real-time 3D location and mapping technology (e.g., CARTO® 3 System or other 3D location and mapping technology), in accordance with the disclosures herein. The cardiac mapping and ablation system 200 may include, but is not limited to include, any of the following components: a console system 201; extra-cardiac sensors 214; reference device constellation 215; energy source 219; and/or catheter(s) 220. The console system 201 may include, but is not limited to include, any of the following components: processing device(s) 202 (processor(s)); local storage 208; visual display device 216; and/or operator interface(s) 218. Certain elements of the cardiac mapping and ablation system 200 may be used directly on, in, and/or in proximity to the patient 205 in order to gather information to be used for visualization, diagnostics, and to perform ablation therapy. This information may be provided to the console system 201 for processing, visualization and operator control and direction, some of which is described below.

The reference device constellation 215 (e.g., may be referred to as a location pad) may include a ring of computer-controlled (e.g., controlled by processing device(s) 202) magnets positioned beneath the patient 205. The magnets may have known and fixed strength and position values that may be used as point of origin references for the magnetic fields in the surrounding space and may provide the reference information to the processing device(s) 202 to be used in producing accurate 3D images of the heart.

The extra-cardiac sensor(s) 214 may be electrodes on the skin of a patient 205, for example. The extra-cardiac sensor(s) 214 may detect the electrical activity of the heart via detection of electrical changes on the skin due to the electro-physiologic pattern of the heart, and provide information on the electrical activity to the processing device(s) 202 to be used in diagnosing arrhythmias and determining a therapeutic course of action. Processed versions of the extra-cardiac signals detected by the extra-cardiac sensor(s) 214 may be displayed on visual display device 216, for example in a graphical user interface (GUI).

One or more devices may be used on the patient 205 for therapeutic and diagnostic purposes. In the example cardiac mapping and ablation system 200, catheter(s) 220 are shown and described for these purposes; however, other devices may be used for diagnostics and/or therapeutic treatment.

One or more catheter(s) 220 may be percutaneously inserted by a physician through the patient's 205 vascular system into the heart of the patient 205. The catheter(s) 220 may be equipped with a variety of sensors, such as location, electrical, pressure, image and/or temperature sensors, for the purpose of gathering information for diagnostic mapping and/or delivering therapeutic treatment (e.g., performing ablation). Different types of catheter(s) 220 may be used including, but not limited to, the following example types: fixed catheter; deflectable catheter; bi-directional catheter; uni-directional catheter; tricuspid mapping catheter; halo-shaped tip catheter; basket catheter; and/or lasso-shaped catheter. When the catheter(s) 220 is used for performing ablation on a target location (e.g., one or more locations along a path), for example by applying RF energy, the catheter(s) 220 may receive the RF energy from the energy source 219, as may be instructed by the processing device(s) 202. In an example, the catheter(s) 220 may request the RF energy directly from the energy source 219.

Figure 2B:
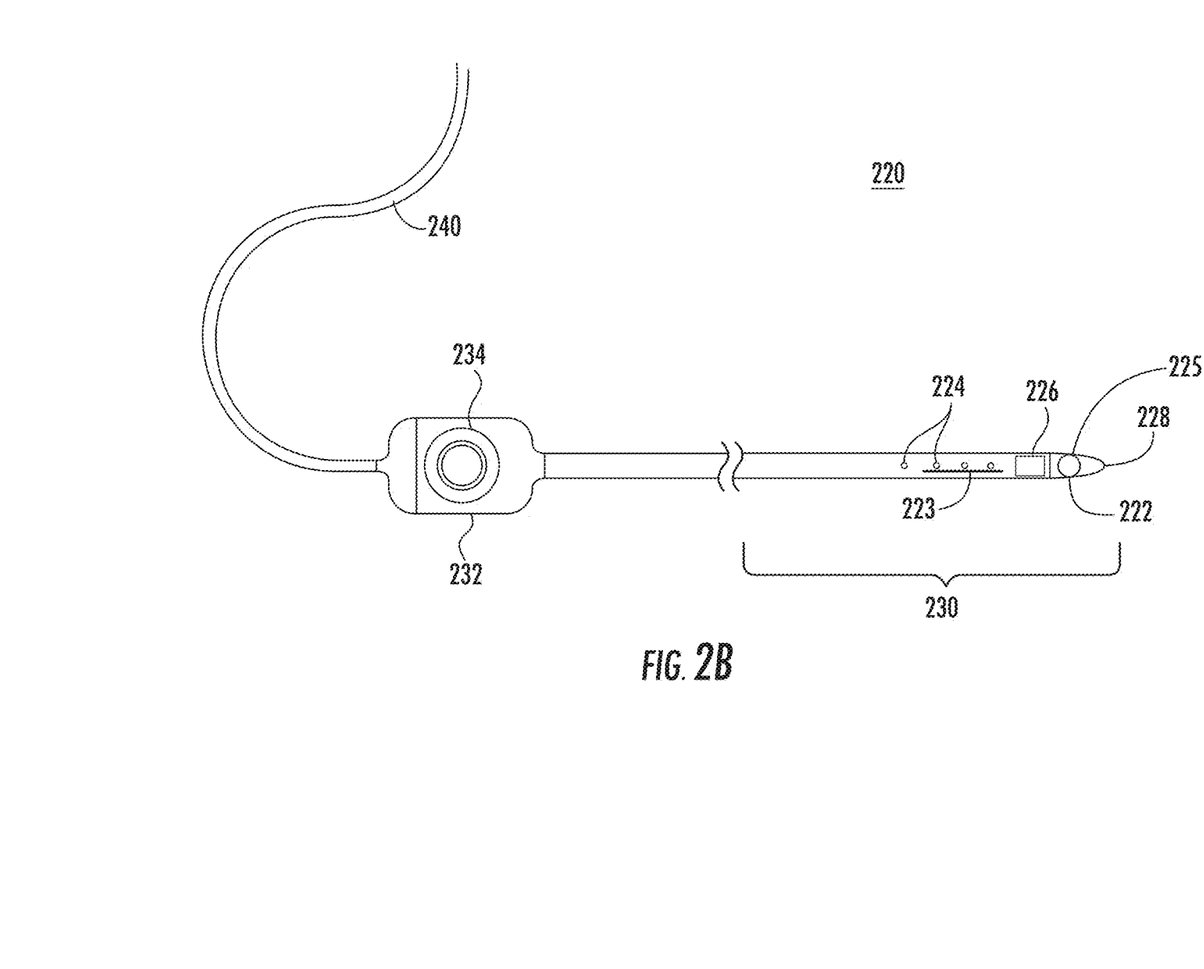
FIG. 2B is a schematic diagram of an example catheter that may be included in the example cardiac mapping and ablation system of FIG. 2A.

An example catheter 220 is shown in greater detail in FIG. 2B, showing some, but not all, of the elements that may be included in the catheter 220. A catheter 220 may include, but is not limited to include, any one or more of the following components: electrode(s) 222; temperature sensor(s) 223; non-contact electrodes 224; image sensor(s) 225; positioning sensor(s) 226; distal tip 228; distal end 230; handle 232; and/or cable 240. The schematic diagram of the catheter 220 in FIG. 2B is a high-level representation of possible components of the catheter 220, such that the location and configuration of the components in catheter 220 may be different than shown.

The distal end 230 of the catheter 220 may include an electrode(s) 222 at the distal tip 228 that may be used to measure electrical properties of the cardiac tissue. The electrode(s) 222 may also be used to send electrical signals to the heart for diagnostic purposes. The electrode(s) 222 may also perform ablation on defective cardiac tissue by applying energy (e.g., RF energy) directly to the cardiac tissue at the desired location of ablation.

The distal end 230 of the catheter 220 may include temperature sensor(s) 223 to measure the temperature of the cardiac tissue in contact with the distal end 230 and/or measure the temperature of the distal end 230 itself. For example, thermocouples or thermistors for measuring temperature may be placed anywhere along the distal end 230 to serve as temperature sensor(s) 223.

The distal end 230 may include non-contact electrodes 224 arranged in an array, which may be used to simultaneously receive and measure far-field electrical signals from the walls of the heart chamber of the patient 205. The electrode(s) 222 and non-contact electrodes 224 provide information regarding the electrical properties of the heart to the processing device(s) 202 for processing.

The catheter(s) 220 may be equipped with one or more image sensor(s) 225, such as a charge coupled device (CCD) image sensor, and/or a camera for capturing endoscopic images when inserted in a body cavity. The image sensor(s) 225 may be located at the distal end 230.

The distal end 230 may include positioning sensor(s) 226 (also called location sensors) in the distal tip 228 of the catheter 220 that may generate signals used to determine the position and orientation (and/or distance) of the catheter 220 in the body. In an example, the relative position and orientation of the positioning sensor(s) 226, the electrode(s) 222, and the distal tip are fixed and known in order to facilitate accurate positioning information of the distal tip. For example, the position of the positioning sensor(s) 226 may be determined in part based on the relative position to known positions outside the heart (e.g., based on extra-cardiac sensors 214). The use of positioning sensor(s) 226 may provide improved location accuracy within the magnetic fields in the surrounding space and provide location information that is adaptable to patient movement because the position information of the catheter 220 is relative to the anatomy of the patient 205.

The handle 232 of the catheter 220 may be operated by the physician and may include controls 234 to enable the physician to effectively steer the distal tip 228 in the desired direction.

The electrodes 222, 224, and sensors 223, 225, 226 may be connected to the processing device(s) 202 via wires that may pass through handle 232 and cable 240, in order to provide information, such as location, electrical, imaging and/or temperature information, to the console system 201, which may be used to operate and display the function of the catheter 220 within the heart in real-time.

With reference to FIG. 2A, within the console system 201, the processing device(s) 202 (e.g., processor(s)) may include one or more signal processing circuits that may be contained inside a computer, for example. The processing device(s) 202 may be implemented in hardware and/or programmed in software to carry out the functions of the cardiac mapping and ablation system 200. This software may be downloaded to the processing device(s) 202 in electronic form, over a network, for example, and/or it may be provided on tangible media, such as magnetic or optical media or other nonvolatile memory. For example, enhancement may be made to the cardiac visualization and diagnostic capabilities of the cardiac mapping and ablation system 200 by downloading and installing software modules to the processing device(s) 202. In an example, processing device(s) 202 may comprise a general-purpose computer.

The processing device(s) 202 may receive, amplify, filter and/or digitize signals (carrying information or data) from catheter 220, including signals generated by the sensors 223, 225, and 226, and electrodes 222 and 224. The signals are received and used by the processing device(s) 202 to compute such data as the position and orientation of the catheter 220, the temperature of the catheter, as well as the electrical characteristics and/or temperature of tissues in the heart chamber. In an example, appropriate circuitry may be associated with the catheter 220 itself so that processing device(s) 202 receive signals that are already amplified, filtered and/or digitized.

The processing device(s) 202 may also be used to generate and send signals, containing information or instructions, to other elements in the cardiac mapping and ablation system 200. For example, the processing device(s) 202 may generate and send real-time 3D cardiac map information for display on the visual display device 216. In another example, the processing device(s) 202 may send/receive information to/from the local storage 208. In another example, the processing device(s) 202 may send signals to the catheter(s) 220 to apply RF energy provided by the energy source 219 to an ablation target.

As explained above, processing device(s) 202 may implement specific functions, which may be represented (e.g., illustratively or physically) as separate units within the processing device(s) 202. For example, the processing device(s) 202 may include a decoder unit 204 (e.g., implemented in hardware as a processing circuit and/or software as a software module) that may be configured to receive signals from sensors in the catheter 220, and may use the signals to calculate position, orientation, distance, temperature and/or electrocardiogram (ECG) values for the catheter distal tip 228.

In another example, the processing device(s) 202 may include a controller unit 207 for sending instructions to other devices in the cardiac mapping and ablation system 200. For example, the controller unit 207 may send instructions to the energy source 219 to provide RF energy to the catheter(s) 220 for ablation, and may send instructions to the catheter(s) 220 to apply the RF energy to an ablation target (e.g., one or more locations along a path).

In another example, the processing device(s) 202 may include a 3D image reconstruction unit 206 (e.g., implemented in hardware as processing circuits and/or software as a software module) that may be configured to collect image data from a medical imaging system (not shown), such as a magnetic resonance imaging (MRI) system and/or a computed tomography (CT) system, as well as image data from the catheter(s) 220 (e.g., from image sensor(s) 225 in FIG. 2B). 3D image reconstruction unit 206 may use the image data to construct a simulated surface of the patient's 205 cardiac chamber and provide it to the visual display device 216 for display.

The processing units 204, 206 and 207 are examples, and do not comprise all the possible functions that may be implemented in processing device(s) 202. Other functionality and/or processing units may be included in processing device(s) 202 but are not shown.

Visual display device 216 may be used to display 2D and/or 3D visual representations and/or maps of the heart and show the exact location and orientation of the catheter 220 within the heart, based on information processing done in the processing device(s) 202. For example, maps may be displayed as anatomical maps, cardiac electrical activation maps, cardiac electrical propagation maps, cardiac electrical potential maps, impedance maps, cardiac chamber geometry, and ECG fragmentation maps.

In addition to the cardiac representations/maps and catheter(s), other objects in view and/or information (e.g., labels, diagnostics etc.) relevant to the mapping, diagnostic and therapeutic procedures may also be displayed on visual display device 216. The 3D visual representation of the cardiac mapping is a critical tool used by the physician to provide an accurate and real-time visual guide for performing diagnostic and therapeutic cardiac procedures, such as cardiac ablation.

The operator interface(s) 218 may be used by one or more operators to interact with and control the cardiac mapping and ablation system 200. The operator interface(s) 218 may include, but are not limited to include, the following devices: a keyboard; a touch-sensitive display; and/or a mouse. The operator interface(s) 218 may allow operators to access and manipulate visual information, and may provide them with the ability to change views, and tag and/or label lesions to keep track of treatment strategies for individual patients.

Operators of the cardiac mapping and ablation system 200 may include, but are not limited to include, the following: a physician (e.g., an electrophysiologist) who may, for example, control the catheter, gather and interpret diagnostics, and perform the ablation procedure; and a Clinical Application Specialist (CAS) who functions as the physician's assistant during the procedures.

A cardiac mapping and ablation system, such as the cardiac mapping and ablation system 200 in FIG. 2A, may provide information on the electrical activity and/or temperature of the cardiac system and/or the devices, such as catheters, in contact with the cardiac system, and may visually display this information on the 3D map. For example, electrical signals of cardiac tissue may be measured by sensors/electrodes placed near and/or in direct contact with the cardiac tissue (e.g., extra-cardiac sensor(s) 214 in FIG. 2A and/or electrode(s) 222 on catheter 220 in FIG. 2B) and displayed in real time in the 3D cardiac map. The electrical activation sequence resulting from the local activation times (LATs) of different zones in the cardiac chamber may be displayed in the 3D cardiac map using colors to show electrical waves from start to finish (e.g., red indicates the earliest LAT, purple indicates the latest LAT, and other colors in the color spectrum indicate the LATs in between). Similarly, color may be used to show temperature of the cardiac tissue and or the temperature of devices such as the catheter, which becomes hot when performing ablation. For example, red may indicate hot temperatures (e.g., 60° C.), blue may indicate cold temperatures (e.g., 30° C.), and other colors in the color spectrum indicate temperatures in between.

As described above, a 3D cardiac mapping and ablation system, such as the CARTO® system, can display complicated cardiac maps with numerous anatomical features, objects, points, tags and a wide spectrum of colors. For example, points may show a pairing of an anatomical position and intra-cardiac ECG at a specified point in time, tags may be used by the physician to label particular points and locations for reference, and colors may be used to show temperature and/or electrical activity.

When using these 3D cardiac maps during therapeutic or diagnostics procedures, there are instances where a physician may need to focus on a subset of the visual information in the 3D cardiac map in order to effectively complete a task, such that other visual information acts as visual noise and hinders the physician's view of the procedure. For example, when ablation is being performed, the physician may need to focus on the catheter position relative to the surrounding cardiac tissue and the temperature distribution on the 3D map, and thus would have a better view with some of the other visual information removed. In another example, the catheter temperature distribution may be color-coded using colors, such as red, yellow and green, that are also used in the 3D cardiac map (e.g., to show electrical activity, temperature of the cardiac tissue, etc.), making it difficult for the physician to identify and distinguish the catheter temperature distribution from the surrounding 3D cardiac map.

A tool a physician may use to assist in removing some of the visual noise in the 3D visualization is map transparency; however, map transparency lacks anatomical detail and may hinder the physician's ability to understand the surrounding anatomy. In fact, transparent maps may not be well-suited to applications where visual details of the anatomy are needed, such as may be the case during ablation.

Additionally, in order to remove unwanted visual information from the 3D map when it is not needed, existing systems require a physician to manually work through multiple menus to filter out the excess data, which may be complex, unintuitive and time-consuming. Thus, it is desirable for physicians to have a convenient and accessible solution for visualizing particular temperature distributions and/or points of interest in a 3D cardiac map and removing extraneous visual noise when needed.

The disclosures are described herein with respect to cardiac mapping and ablation procedures for the cardiac system, although it is understood by one skilled in the art that the disclosures may be applied to systems and procedures that can be used in any cavity or system in the body, including, but not limited to, the respiratory/pulmonary system, the respiratory and pulmonary system, the digestive system, the neurovascular system, and/or the circulatory system.

In accordance with the disclosures herein, a system and method provides a physician or operator with the ability to select, using for example a button or menu, a simplified and/or clarified level of visualization data in the 3D view of a cardiac procedure, referred to as a "glass state" or "dim state" view, by filtering out unwanted visual data (e.g., points, tags, and/or colors) and/or adding edge enhancement to the cardiac anatomy. The visualization data removed and maintained in the glass state view may be defined by or tailored to a physician's viewing preferences, for example. Glass state functionality in a cardiac mapping and ablation system provides a quick and efficient way for physicians to focus on a subset of the visual data when performing a cardiac procedure and remove visual data that is hindering the physician's view.

As part of the disclosed cardiac mapping and ablation system, the glass state view may be implemented to include adding edge enhancement, referred to as a "glass view", to the cardiac anatomy in a visual 3D cardiac map (e.g., as displayed in visual display device 216 of cardiac mapping and ablation system 200 in FIG. 2A). The glass view may be applied to the 3D cardiac image and provides well-defined visibility of the details of the cardiac anatomy on the 3D cardiac map by highlighting the anatomical features, as illustrated in FIG. 3.

Figure 3:
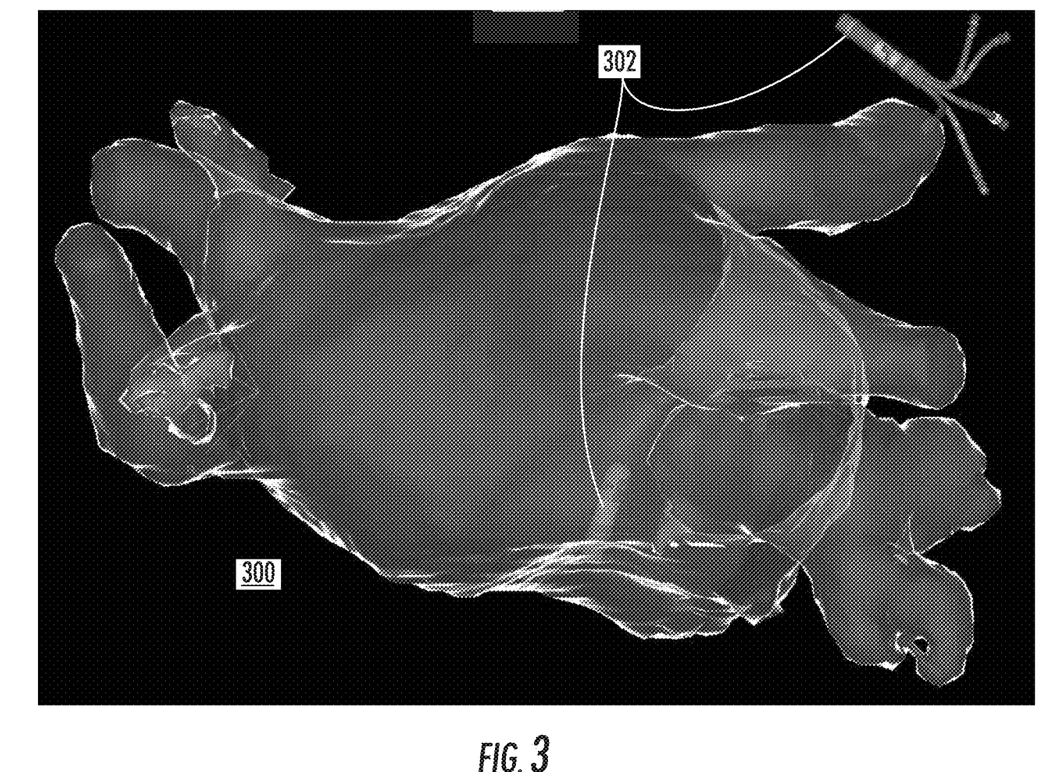
FIG. 3 is a 3D image of an example 3D cardiac map, corresponding to the 3D cardiac map in FIG. 1, with an added glass view.

FIG. 3 is an example 3D cardiac map 300, corresponding to the 3D cardiac map 100 in FIG. 1, with an added glass view, and showing the location and orientation of catheters 302. The glass view provides a type of transparent view with shading or edge enhancement that can retain coloring information (e.g., color showing temperature distribution, electrical activity, etc.), if desired by the physician. With the glass view, catheters 302 may be easier to see in the 3D cardiac map 300 while retaining the desired level of coloring distribution data. The glass view enables simultaneous viewing of multiple sides of the 3D anatomical cardiac structure because the 3D cardiac map 300 with glass view can be rotated.

Figure 4A:
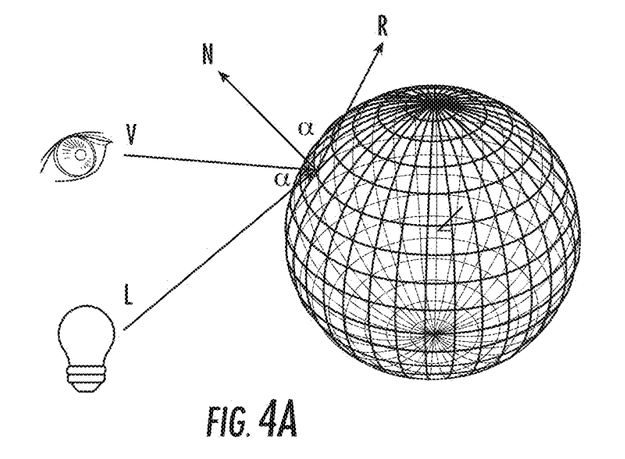
FIGS. 4A, 4B and 4C illustrate an example method to add a glass view to a 3D image of a sphere by adding shading to the surface of the 3D image.
Figure 4B:
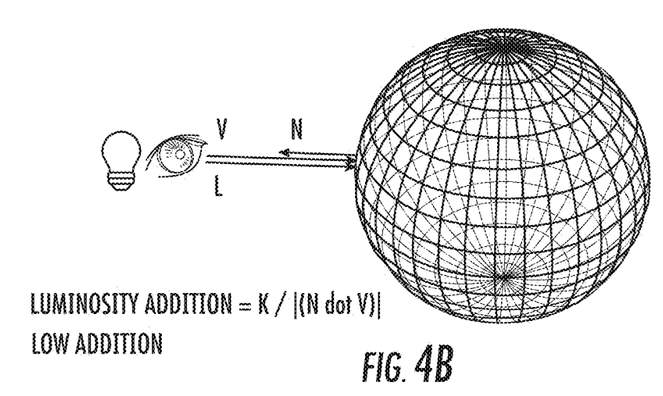
Figure 4C:
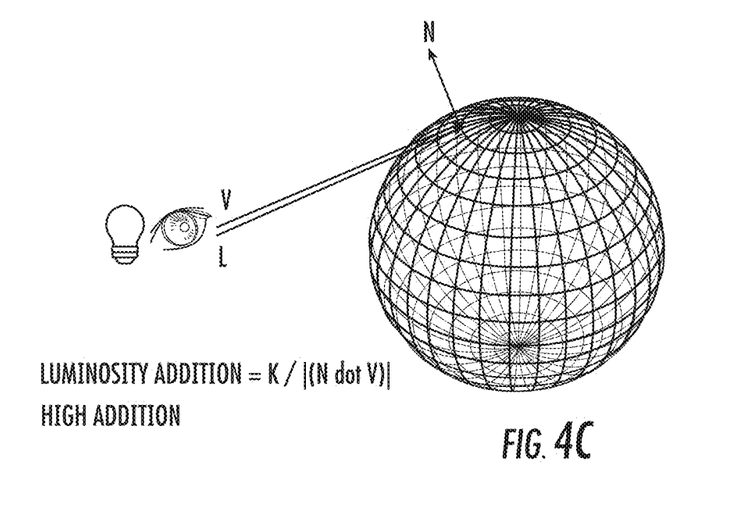

FIGS. 4A, 4B and 4C illustrate an example method to add a glass view to a 3D image of a sphere by adding shading to the surface of the 3D image (the same method can be applied to a 3D cardiac image or other anatomical image, and can be used to generate the glass view cardiac map 300 in FIG. 3). Considering a point x on the surface of the 3D image, vector V is the viewing path from the viewpoint (e.g., from an operator looking at the visual display of the 3D image), vector L is the path of light from the light source (the light source/light path does not affect the luminosity addition), vector R is the path of the reflected light, and vector N is the normal vector (i.e., normal or perpendicular to the point on the 3D image). The angle α between the light path L and the normal vector N is the same as the angle α between the reflected path R and the normal vector N.

To generate the glass view, a luminosity value (e.g., corresponding to light, shading, white color, or other color) is generated and added to each point on the surface of the 3D image according to the following equation:

$$\text{Luminosity Value} = \frac{K}{|N \cdot V|} \quad \text{Equation 1}$$

where K is a small constant (e.g., 0.00001). In the case shown in FIG. 4B, vectors L and V come from the same place (i.e., the light source is at the same location as the viewpoint), and the normal vector N is directed to the viewpoint. Because the vectors N and V are the same or almost the same, then the vector product $|N \cdot V|$ is equal to or close to 1, and the luminosity addition value is very low because constant K is small. In the case shown in FIG. 4C, vectors L and V also come from the same place, but the normal vector N is perpendicular or almost perpendicular to the view path V. In this case, the vector product $|N \cdot V|$ is almost 0, and the luminosity value addition value is high. If the vector product $|N \cdot V|$ result is 0, then the luminosity addition value may be set to the maximum luminosity value (e.g., for white addition, the value corresponds to pure white). In an example, the luminosity addition values are normalized between 0 and 1, where 1 is the maximum luminosity value (e.g., pure white) and 0 means no luminosity (color) is added to the point in the 3D image.

As part of the disclosed cardiac mapping and ablation system, the glass state view may be implemented to include removal of visual noise from the 3D cardiac map, leaving the shape of the cardiac anatomy so that the physician can easily see the catheter behind the map. The disclosed glass state view may be implemented to further include maintenance of a desired amount of color-coded data (e.g., color-coded temperature information) in the 3D cardiac map. In an example, only a portion of the color-coded information in the 3D cardiac map may be removed when the glass state view is selected. In an example, the disclosed glass state view may reduce or remove excess coloring information in the 3D cardiac map by converting the coloring (e.g., LAT color-coding, temperature color-coding, etc.) to grey-scale or shaded, low-density coloring. In an example, excess coloring may be removed entirely, depending on the visualization needs of the physician.

The glass state view reduces the visual noise by reducing visual data such as the amount of coloring and/or the number of points and tags in the 3D cardiac map. Extraneous visual data on the 3D cardiac map is filtered out to enable the physician to focus on critical visual information easily and quickly. Moreover, the physician does not need to work through multiple menus filter the excess data out because the glass state view is pre-programmed so that it can be instantly activated or deactivated, for example via an button or menu accessible to the physician. In an example, two or more different glass state views may be made available to the physician (e.g., via a selectable menu). For example, a first glass state view may include the glass view, the catheter, and temperature color-coding visual data while removing all other points, objects and tags, and a second glass state view may similarly include the glass view and catheter but show a grey-scale cardiac map with temperature color-coding information removed.

As an example of visual noise reduction, the glass state view may hide all data points (e.g., tags, labels, etc.) that have not been selected by the physician or operator, and display the selected points and one or more catheters within the 3D cardiac map. As stated above, the glass state view may also add a glass view to the cardiac anatomy.

The disclosed glass state view implemented in a cardiac mapping and ablation system (e.g., cardiac mapping and ablation system 200 in FIG. 2A) provides the physician with an improved view of the catheter and anatomical visual information needed to perform a particular cardiac procedure and focus on selected points of interest. Examples of catheter and anatomical visual information that may be useful in the glass state view include, but are not limited to, any of the following visual information: the catheter tip; electrode numbers on the catheter; deflection and tissue proximity indications (TPIs) (i.e., change in visualization to indicate that a catheter's electrode is touching cardiac tissue) inside the reconstruction of the 3D cardiac image; and/or color-coded temperature information.

Figure 5:
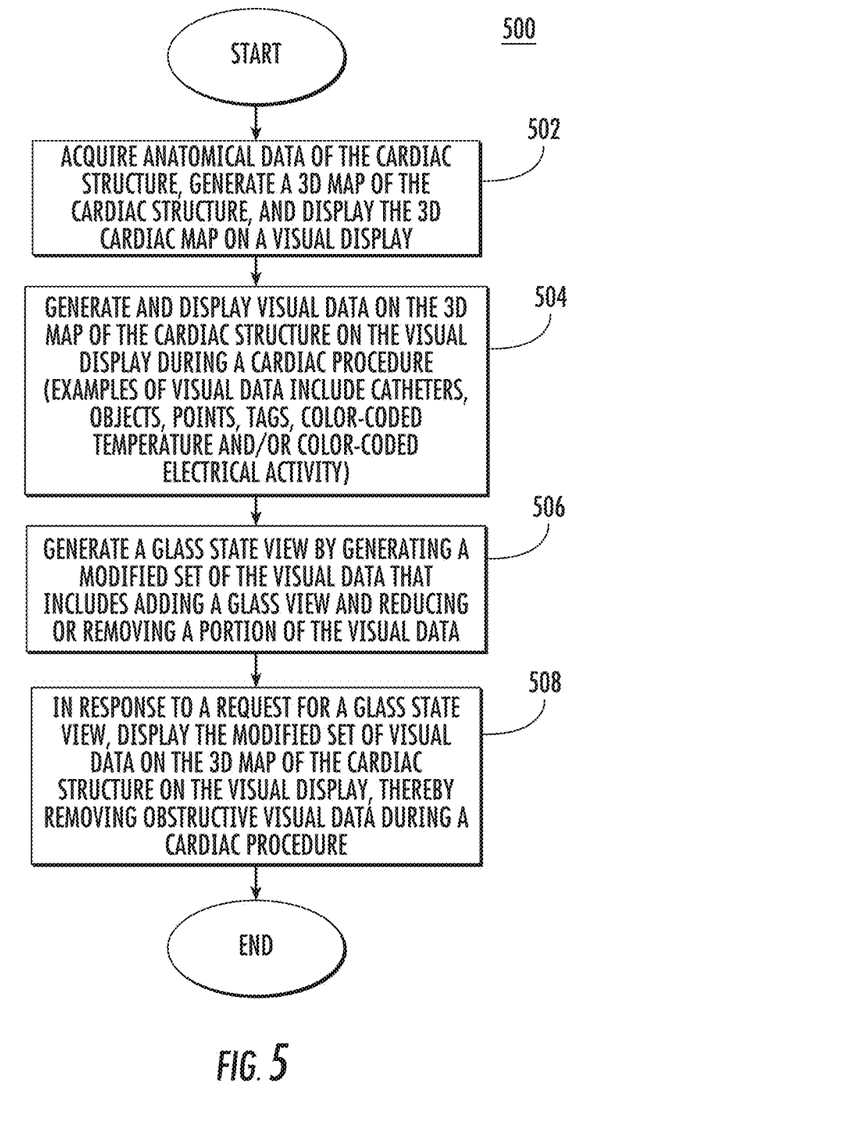
FIG. 5 is a flow diagram of an example visual noise reduction with glass view procedure for implementing a glass state view in real-time 3D cardiac imaging, as may be used in a cardiac mapping and ablation system.

FIG. 5 is a flow diagram of an example visual noise reduction with glass view procedure 500 for implementing a glass state view in real-time 3D cardiac imaging, as may be used in a cardiac mapping and ablation system. At 502, anatomical data of the cardiac structure may be acquired and used to generate a 3D map (model or image) of the cardiac structure and display the 3D map on a visual display. For example, the 3D model of the cardiac structure may be generated using a real-time 3D cardiac location and mapping system such as the CARTO® 3 System.

At 504, visual data may be generated and displayed on the 3D map of the cardiac structure during a cardiac procedure (e.g., a diagnostic or therapeutic cardiac procedure such as mapping and ablation). Examples of visual data may include, but are not limited to include, the following information: objects (e.g., catheters, other devices, 3D synthetic heart model, etc.); points and/or tags (e.g., points to identify points of interest that may be automatically added by the system or added manually by the operator); and/or color-coding information (e.g., to show electrical activity, anatomical temperature, device temperature, etc.). At 506, at least one glass state view is generated by generating a modified set of visual data that may include adding a glass view (e.g., using the method described in FIGS. 4A-4C) and reducing or removing unwanted visual data such as points, objects, tags and/or color-coding information, from the 3D cardiac map. For example, the visual data that is removed may correspond to points, objects, and/or color-coding information that have not been selected or tagged by the physician.

In an example, the modified set of visual data included in the glass state view may be based on a default setting or may be tailored to the physician's preferences. For example, the physician may provide input to the system to define what visual data should be included in the glass state view. For example, with reference to FIG. 2A, a physician (or CAS) may use operator interface(s) 218 to provide one the preferred visual data to be included in the glass state view to processing device(s) 202 to be used by the 3D image reconstruction unit 206. The preferred visual data may be stored in console system 201 in local storage 208, for example.

With reference to FIG. 5, at 508, in response to a request for a glass state view (e.g., from an operator), the requested glass state view may be displayed on the visual display device, thereby removing obstructive visual data during a cardiac procedure. The example visual noise reduction with glass view procedure 500 may be implemented in the cardiac mapping and ablation system 200 of FIG. 2A. For example, with reference to FIG. 2A, the visual noise reduction with glass view procedure may be implemented in 3D image reconstruction unit 206 (e.g., implemented in hardware as processing circuits and/or software as a software module) and may be activated by the physician via operator interfaces 218, for example by selecting a button visually displayed in the visual display device 216.

Figure 6A:
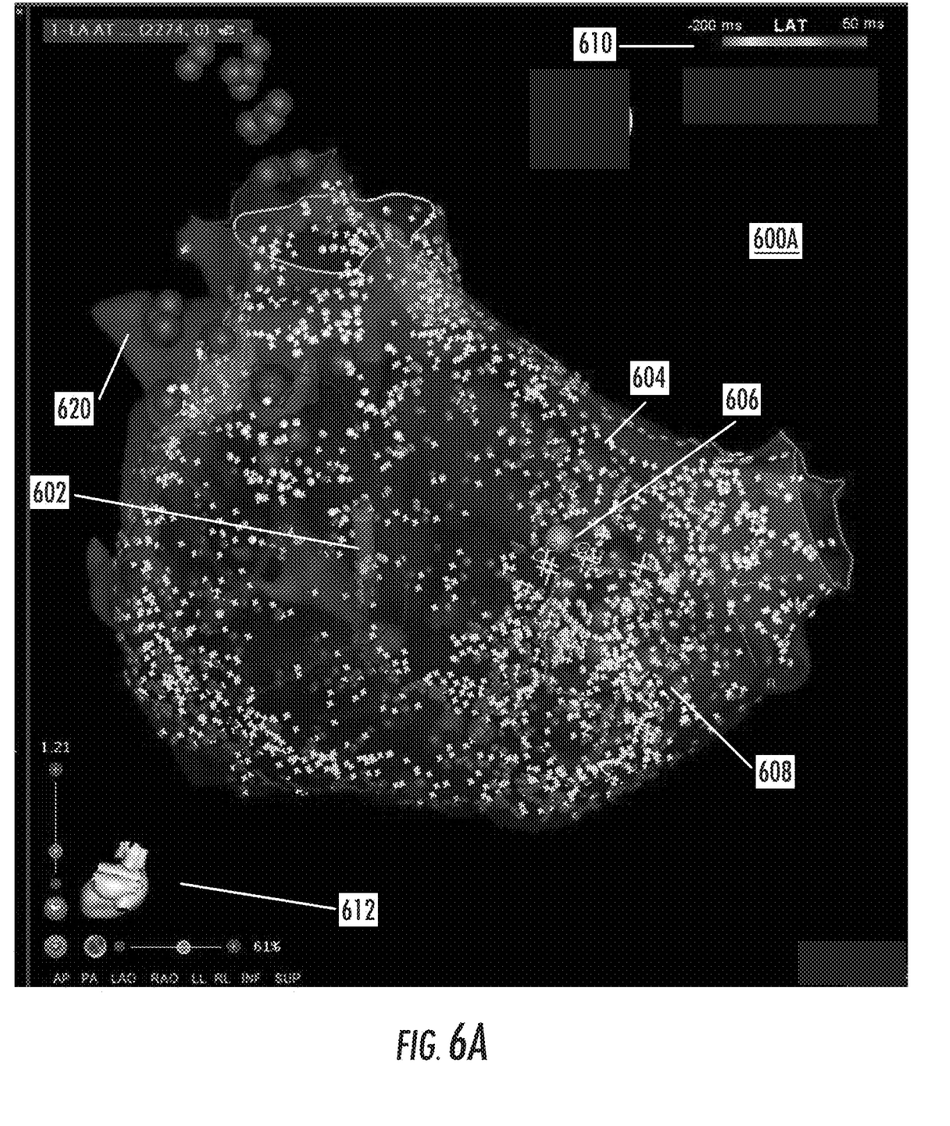
FIG. 6A is an example 3D cardiac map including visual data and FIG. 6B is a corresponding 3D cardiac map with glass state view activated including a glass view and reduced visual data.

FIG. 6A is an example 3D cardiac map 600A including such visual data as the catheter 602, points 604 (shown by white crosses), projected points 606 on the reconstruction (shown by colored oblate spheroids), tags 608 corresponding to points tagged by the operator (shown by large spheres), color-coding showing the LATs 610, and a 3D synthetic heart model 612 used for orientation. The abundance of visual data in FIG. 6A partially obscures the view of the catheter 602, which may hinder the physician's ability to perform an accurate procedure. Moreover, the details of the surface of the cardiac structure are not easy to see. For example, the left atrial appendage (LAA) 620 in the cardiac anatomy is hard to distinguish from the surrounding visual data.

Figure 6B:
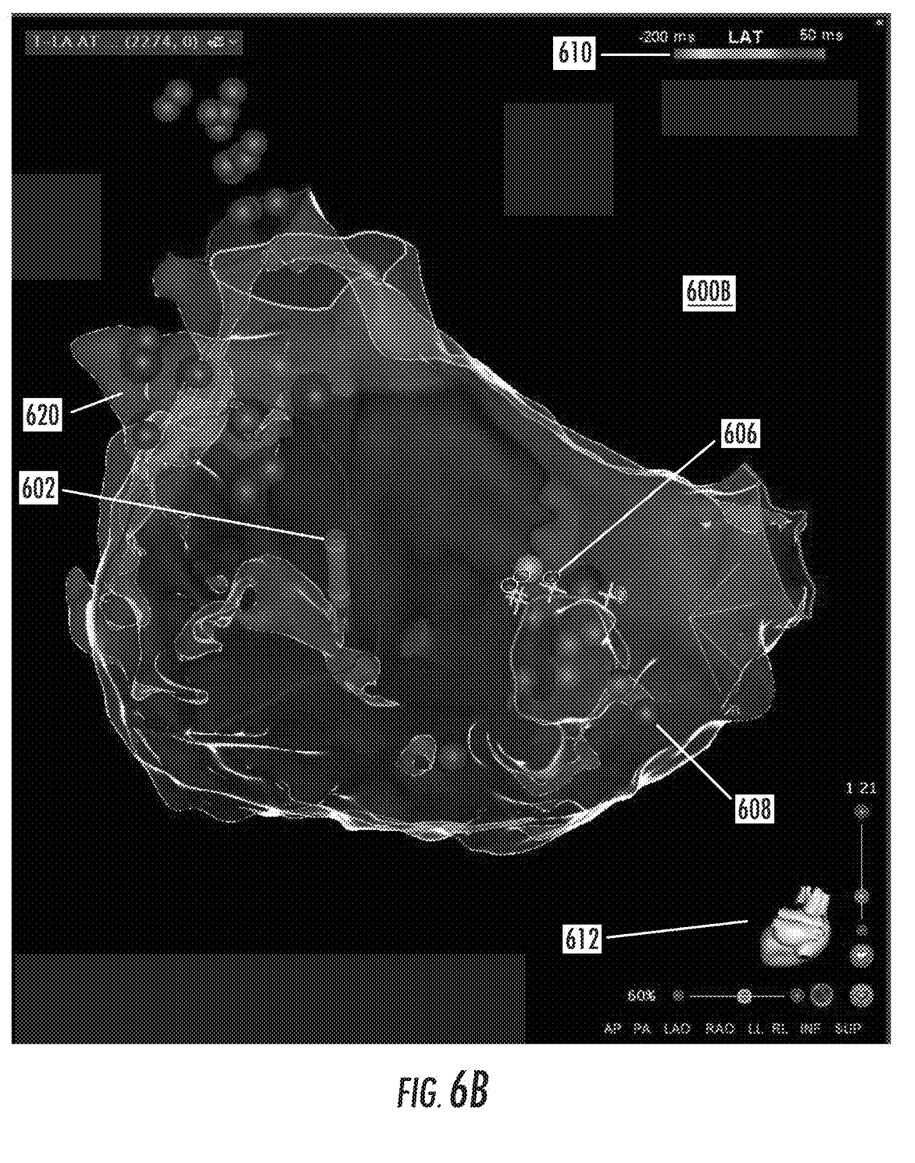

FIG. 6B is an example 3D cardiac map 600B with glass state view activated, corresponding to the 3D cardiac map 600A. In the glass state view shown in FIG. 6B, visual data including points 604 and some projected points 606 have been removed, and a glass view has been added to provide shading to the cardiac anatomy. In the 3D cardiac map 600B, the LAA 620 and the catheter 602 are much more visible with the addition of the glass view and with obstructing visual data removed. The color-coding information showing the LATs 610 has been maintained in the glass state view, however, it may alternatively be removed. In comparison to the cardiac map 600A in FIG. 6A with an abundance of visual noise data, the cardiac map 600B in FIG. 6B provides improved visibility of the catheter with respect to the surrounding cardiac anatomy, thus making it easier for a physician to view and accurately perform a cardiac procedure such as ablation.

The embodiments and procedures described herein may be implemented in hardware, and/or software. A computer system for performing ablation may be capable of running software modules that introduce additional features including the procedures described herein. The procedures described herein may enable advanced cardiac visualization, and diagnostic capabilities to enhance clinicians' ability to diagnose and treat heart rhythm disorders. Although the procedures disclosed herein are describe with respect to ablation procedures relating to the cardiac system, the systems and procedures disclosed herein may be similarly used as part of therapeutic and diagnostic procedures in other parts of the body.

What is claimed is:

1. A real-time three-dimensional (3D) cardiac imaging system comprising:
a processing device configured to acquire anatomical data of a cardiac structure and generate a 3D model of the cardiac structure;
the processing device configured to generate visual data during a cardiac procedure, wherein the visual data includes tags corresponding to locations tagged by an operator, location and orientation of a catheter, points of interest, and at least one of: color-coded temperature information of the cardiac structure; color-coded temperature information of the catheter; or color-coded local activation times (LAT) for the cardiac structure;
a visual display device configured to visually display the visual data superimposed on the 3D model of the cardiac structure;
the processing device configured to generate a first glass state view by generating a first modified set of the visual data that includes:
removing, based on first pre-programmed viewing preferences of the operator, all the tags, all the points of interest, and at least a portion of the visual data that obscures a view of at least one of an anatomical feature or a tip of the catheter,
maintaining the location and orientation of the catheter, and
adding edge enhancement to the 3D model of the cardiac structure; and
in response to a request for the first glass state view, the visual display device configured to visually display the first modified set of the visual data superimposed on the 3D model of the cardiac structure.

2. The real-time 3D cardiac imaging system of claim 1, wherein:
the processing device is further configured to generate the edge enhancement for each point on the 3D model of the cardiac structure by:
calculating a luminosity value proportional to $$\frac{K}{|N \cdot V|},$$

where K is a constant value, N is a normal vector at the point on the 3D model of the cardiac structure, and V is a vector representing a viewing path from a viewpoint to the point on the 3D model of the cardiac structure; and
adding the luminosity value to the point in the 3D model of the cardiac structure.

3. The real-time 3D cardiac imaging system of claim 1, wherein:
the processing device is further configured to generate a second glass state view by generating a second modified set of the visual data that includes removing, based on second pre-programmed viewing preferences of the operator, at least a portion of the visual data that obscures a view of the at least one of the anatomical feature or the tip of the catheter and is different from the first glass state view and the first modified set of the visual data, respectively.

4. The real-time 3D cardiac imaging system of claim 1, wherein the visual data includes at least the color-coded temperature information of the cardiac structure, and the first modified set of the visual data maintains all the color-coded temperature information of the cardiac structure from the visual data.

5. The real-time 3D cardiac imaging system of claim 1, wherein the visual data includes at least the color-coded temperature information of the cardiac structure, and the generating the first modified set of the visual data includes converting coloring of the color-coded temperature information of the cardiac structure in the visual data to greyscale or shaded, low-density coloring.

6. The real-time 3D cardiac imaging system of claim 1, wherein the removing the at least a portion of the visual data includes removing obstructive visual data that obstructs a view of the tip of the catheter and surrounding cardiac anatomy to the tip of the catheter during the cardiac procedure.

7. The real-time 3D cardiac imaging system of claim 1, further comprising:
an operator interface configured to receive, from the operator, the request for the first glass state view and provide the request for the first glass state view to the processing device.

8. The real-time 3D cardiac imaging system of claim 1, further comprising:
an operator interface configured to receive, from the operator, the first pre-programmed viewing preferences of the operator for the first glass state view and provide the first pre-programmed viewing preferences of the operator to the processing device; and
wherein the processing device is further configured to define visual information to be included in the first modified set of the visual data based on the first pre-programmed viewing preferences of the operator.

9. The real-time 3D cardiac imaging system of claim 1 implemented as part of a cardiac mapping and ablation system.

10. A method for real-time three-dimensional (3D) cardiac imaging, performed by a real-time 3D cardiac imaging system, the method comprising:
acquiring anatomical data of a cardiac structure and generating a 3D model of the cardiac structure;
generating visual data during a cardiac procedure, wherein the visual data includes tags corresponding to locations tagged by an operator, and location and orientation of a catheter, points of interest, and at least one of: color-coded temperature information of the cardiac structure; color-coded temperature information of the catheter; or color-coded local activation times (LAT) for the cardiac structure;
visually displaying, on a visual display device, the visual data superimposed on the 3D model of the cardiac structure;
generating a first glass state view by generating a first modified set of the visual data that includes:
removing, based on first pre-programmed viewing preferences of the operator, all the tags, all the points of interest, and at least a portion of the visual data that obscures a view of at least one of an anatomical feature or a tip of the catheter,
maintaining the location and orientation of the catheter, and
adding edge enhancement to the 3D model of the cardiac structure; and in response to a request for the first glass state view, visually displaying, on the visual display device, the first modified set of the visual data superimposed on the 3D model of the cardiac structure.

11. The method of claim 10, further comprising:
generating the edge enhancement for each point on the 3D model of the cardiac structure by:
calculating a luminosity value proportional to $$\frac{K}{|N \cdot V|},$$

where K is a constant value, N is a normal vector at the point on the 3D model of the cardiac structure, and V is a vector representing a viewing path from a viewpoint to the point on the 3D model of the cardiac structure; and
adding the luminosity value to the point in the 3D model of the cardiac structure.

12. The method of claim 10, further comprising:
generating a second glass state view by generating a second modified set of the visual data that includes removing, based on second pre-programmed viewing preferences of the operator, at least a portion of the visual data that obscures a view of the at least one of the anatomical feature or the tip of the catheter and is different from the first glass state view and the first modified set of the visual data, respectively.

13. The method of claim 10, wherein the visual data includes at least the color-coded temperature information of the cardiac structure, and the first modified set of the visual data maintains all the color-coded temperature information of the cardiac structure from the visual data.

14. The method of claim 10, wherein the visual data includes at least the color-coded temperature information of the cardiac structure, and the generating the first modified set of the visual data includes converting coloring of the color-coded temperature information of the cardiac structure in the visual data to grey-scale or shaded, low-density coloring.

15. The method of claim 10, wherein the removing the at least a portion of the visual data includes removing obstructive visual data that obstructs a view of the tip of the catheter and surrounding cardiac anatomy to the tip of the catheter during the cardiac procedure.

16. The method of claim 10, further comprising:
receiving, from the operator, the request for the first glass state view via an operator interface.

17. The method of claim 10, further comprising:
receiving, from the operator, the first pre-programmed viewing preferences of the operator for the first glass state view via an operator interface; and
defining visual information to be included in the first modified set of the visual data based on the first pre-programmed viewing preferences of the operator.

18. The method of claim 10, wherein the real-time 3D cardiac imaging system is implemented as part of a cardiac mapping and ablation system.

* * * * *

UNITED STATES PATENT AND TRADEMARK OFFICE
CERTIFICATE OF CORRECTION

PATENT NO. : 10,952,795 B2
APPLICATION NO. : 15/638886
DATED : March 23, 2021
INVENTOR(S) : Benjamin Cohen et al.

It is certified that error appears in the above-identified patent and that said Letters Patent is hereby corrected as shown below:

In the Specification
In Column 1, Lines 22-23, delete "to the to the" and insert -- to the --, therefor.
In Column 1, Line 47, delete "FIG. 1 is" and insert -- FIG. 1 is an --, therefor.
In Column 9, Line 6, delete "an button" and insert -- a button --, therefor.
In Column 10, Line 5, delete "one the" and insert -- one of the --, therefor.

In the Claims
In Column 12, Line 16, in Claim 6, delete "the removing the" and insert -- removing the --, therefor.
In Column 14, Line 11, in Claim 15, delete "the removing the" and insert -- removing the --, therefor.

Signed and Sealed this
First Day of November, 2022

Katherine Kelly Vidal
*Director of the United States Patent and Trademark Office*